US006641540B2

(12) United States Patent
Fleischman et al.

(10) Patent No.: US 6,641,540 B2
(45) Date of Patent: Nov. 4, 2003

(54) MINIATURE ULTRASOUND TRANSDUCER

(75) Inventors: Aaron J. Fleischman, University Heights, OH (US); Shuvo Roy, Cleveland, OH (US); Geoffrey R. Lockwood, Kingston (CA)

(73) Assignee: The Cleveland Clinic Foundation, Cleveland, OH (US)

( * ) Notice: Subject to any disclaimer, the term of this patent is extended or adjusted under 35 U.S.C. 154(b) by 12 days.

(21) Appl. No.: 09/948,068

(22) Filed: Sep. 6, 2001

(65) Prior Publication Data

US 2002/0077551 A1 Jun. 20, 2002

Related U.S. Application Data

(60) Provisional application No. 60/250,775, filed on Dec. 1, 2000.

(51) Int. Cl.[7] .................................................. A61B 8/14

(52) U.S. Cl. ....................... 600/459; 600/462; 600/466; 73/587

(58) Field of Search .................................. 600/437–472

(56) References Cited

U.S. PATENT DOCUMENTS

| | | | | |
|---|---|---|---|---|
| 4,917,097 A | | 4/1990 | Proudian, deceased et al. | |
| 5,167,233 A | | 12/1992 | Eberle et al. | |
| 5,311,095 A | | 5/1994 | Smith et al. | |
| 5,938,615 A | | 8/1999 | Eberle et al. | |
| 6,011,855 A | | 1/2000 | Selfridge et al. | |
| 6,049,158 A | | 4/2000 | Takeuchi et al. | |
| 6,070,468 A | * | 6/2000 | Degertekin et al. | 73/644 |
| 6,151,967 A | * | 11/2000 | McIntosh et al. | 73/514.32 |
| 6,221,015 B1 | | 4/2001 | Yock | |
| 6,246,898 B1 | | 6/2001 | Vesely et al. | |
| 6,328,696 B1 | * | 12/2001 | Fraser | 600/459 |
| 6,328,697 B1 | * | 12/2001 | Fraser | 600/459 |
| 6,443,901 B1 | * | 9/2002 | Fraser | 600/459 |

OTHER PUBLICATIONS

Ladabaum, I., Jin, X., Soh, H.T., Atalar, A., Khuri–Yakub, B.T., Surface Micromachined Capacitive Ultrasonic Transducers, IEEE Transactions on Ultraonics, Ferroelectrics, and Frequency Control, vol. 45, No. 3, May 1998, p. 678–690.*

Jin, X.C.; Ladabaum, I.; Khuri–Yakub, B.T., Surface micromachined capacitive ultrasonic immersion transducers, Micro Electro Mechanical Systems, 1998. MEMS 98. Proceedings., The Eleventh Annual International Workshop on, 1998, p. 649–654.*

Bauer, F.; Simonne, J. J.; and Audaire, L., Ferroelectric Copolymer and IR Sensor Technology Applied to Obstacle Detection, in IEEE, pp. 27–30 (1992).

Fiorillo, A.; Dario, P.; Van Der Spiegel, J.; Domenici, C.; and Foo, J., Spinned P(VDF–TrFE) CoPolymer Layer for a Silicon–Piezoelectric Integrated US Transducer, in Ultrasonics Symposium, pp. 667–670 (1987).

Fiorillo, A. S.; Van Der Spiegel, J.; Bloomfield, P. E.; and Esmail–Zandi, D., A P(VDF–TrFE)–Based Integrated Ultrasonic Transducer, in Sensors and Actuators, pp. 719–725 (1990).

(List continued on next page.)

*Primary Examiner*—Marvin M. Lateef
*Assistant Examiner*—William C. Jung
(74) *Attorney, Agent, or Firm*—Tarolli, Sundheim, Covell & Tummino L.L.P.

(57) ABSTRACT

An ultrasonic transducer (108) for use in medical imaging comprises a substrate (300) having first and second surfaces. The substrate (300) includes an aperture (301) extending from the first surface to the second surface. Electronic circuitry (302) is located on the first surface. A diaphragm (304) is positioned at least partially within the aperture (301) and in electrical communication with the electronic circuitry (302). The diaphragm (304) has an arcuate shape, formed by applying a differential pressure, that is a section of a sphere. A binder material (314) is in physical communication with the diaphragm (304) and the substrate (300).

33 Claims, 12 Drawing Sheets

OTHER PUBLICATIONS

Lockwood, G. R.; Ryan, L. K.; Hunt, J. W. ;and Foster, F. S., Measurement of the Ultrasonic Properties of Vascular Tissues and Blood from 36–65 MHz, in Ultrasound in Med. & Biol., vol. 17, No. 7, pp. 653–666.

Mo, Jian–Hua; Robinson, Andrew L.; Fitting, Dale W.; Terry, Jr., Fred L.; and Carson, Paul L., Micromachining for Improvement of Integrated Ultrasonic Transducer Sensitivity, in IEEE Transactions on Electron Devices, vol. 37, No. 1, pp. 134–139 (1990).

Mo, Jian–Hua; Fowlkes, J. Brian; Robinson, Andrew L.; and Carson, Paul L., Crosstalk Reduction with a Micromachined Diaphragm Structure for Integrated Ultrasound Transducer Arrays, in IEEE Transactions on Ultrasonics, Ferroelectrics, and Frequency Control, vol. 39, No. 1, pp. 48–53 (1992).

Seip, Ralf; VanBaren, Philip; and Ebbini, Emad S., Dynamic Focusing in Ultrasound Hyperthermia Treatments Using Implantable Hydrophone Arrays, in IEEE Transactions on Ultrasonics, Ferroelectrics, and Frequency Control, vol. 41, No. 5, pp. 706–713 (1994).

Sherar, M. D. and Foster, F. S., The Design and Fabrication of High Frequency Poly(Vinylidene Fluoride) Transducers, in Ultrasonic Imaging, vol. 11, pp. 75–94 (1989).

Sleva, Michael Z.; Hunt, William D.; and Briggs, Ronald D., Focusing Performance of Epoxy– and Air–Backed Polyvinylidene Fluoride Fresnel Zone Plates, in J. Acoust. Soc. Am., vol. 96, No. 3, pp. 1627–1633 (1994).

Swartz, Robert G. and Plummer, James D., Integrated Silicon–PVF2 Acoustic Transducer Arrays, in IEEE Transactions on Electron Devices, vol. ED–26, No. 12, pp. 1921–1931 (1979).

Waller, D. and Safari, A., Corona Poling of PZT Ceramics and Flexible Piezoelectric Composites, in Ferroelectrics, vol. 87, pp. 189–195 (1988).

Sleva, Michael Z.; Briggs, Ronald D.; and Hunt, William D., A Micromachined Poly(vinylidene Fluoride–trifluoroethylene) Transducer for Pulse–Echo Ultrasound Applications, in IEEE Transactions on Ultrasonics, Ferroelectrics, and Frequency Control, vol. 43, No. 2, pp. 257–262, Mar. 1996.

* cited by examiner

MINIATURE ULTRASOUND TRANSDUCER

This application claims the benefit of Provisional Application No. 60/250,775, filed Dec. 1, 2000.

FIELD OF THE INVENTION

The invention relates generally to an ultrasound transducer, and more particularly, to a miniature ultrasound transducer fabricated using microelectromechanical system (MEMS) technology.

BACKGROUND OF THE INVENTION

Ultrasound transducers use high-frequency sound waves to construct images. More specifically, ultrasonic images are produced by sound waves as the sound waves reflect off of interfaces between mechanically different structures. The typical ultrasound transducer both emits and receives such sound waves.

It is known that certain medical procedures do not permit a doctor to touch, feel, and/or look at tumor(s), tissue, and blood vessels in order to differentiate therebetween. Ultrasound systems have been found to be particularly useful in such procedures because the ultrasound system can provide the desired feedback to the doctor. Additionally, such ultrasound systems are widely available and relatively inexpensive.

However, present ultrasound systems and ultrasound transducers tend to be rather physically large and are therefore not ideally suited to all applications where needed. Moreover, due to their rather large size, ultrasound transducers cannot be readily incorporated into other medical devices such as, for example, catheters and probes. Hence, an ultrasound system and, more particularly, an ultrasound transducer of a relatively small size is desirable. MEMS technology is ideally suited to produce such a small ultrasonic transducer.

SUMMARY OF THE INVENTION

The present invention is an ultrasonic transducer for use in medical imaging. The ultrasonic transducer comprises a substrate having first and second surfaces. The substrate includes an aperture extending from the first surface to the second surface. Electronic circuitry is located on the first surface. A diaphragm is positioned at least partially within the aperture and in electrical communication with the electronic circuitry. The diaphragm has an arcuate shape that is a section of a sphere. The transducer further comprises a binder material in physical communication with the diaphragm and the substrate.

In accordance with another aspect of the present invention, a method of forming an ultrasonic transducer is provided. The method comprises the steps of providing a substrate with an aperture, covering the aperture with a film, and applying a differential pressure across the film to form a diaphragm having a shape that is a section of a sphere. The method further comprises the step of applying binding material to the diaphragm to maintain the spherical section shape of the diaphragm.

In accordance with another aspect, the present invention is a medical device for insertion into a mammalian body. The medical device comprises an insertable body portion and an ultrasonic transducing section on the body portion. The ultrasonic transducing section has a plurality of ultrasonic transducers. Each of the plurality of ultrasonic transducers comprises a substrate having first and second surfaces. The substrate includes an aperture extending from the first surface to the second surface. Electronic circuitry is located on the first surface. A diaphragm is located at least partially within the aperture and in electrical communication with the electronic circuitry. The diaphragm has an arcuate shape that is a section of a sphere. Each ultrasonic transducer further comprises a binder material in physical communication with the diaphragm and the substrate.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF ILLUSTRATED EMBODIMENTS

Figure 1:
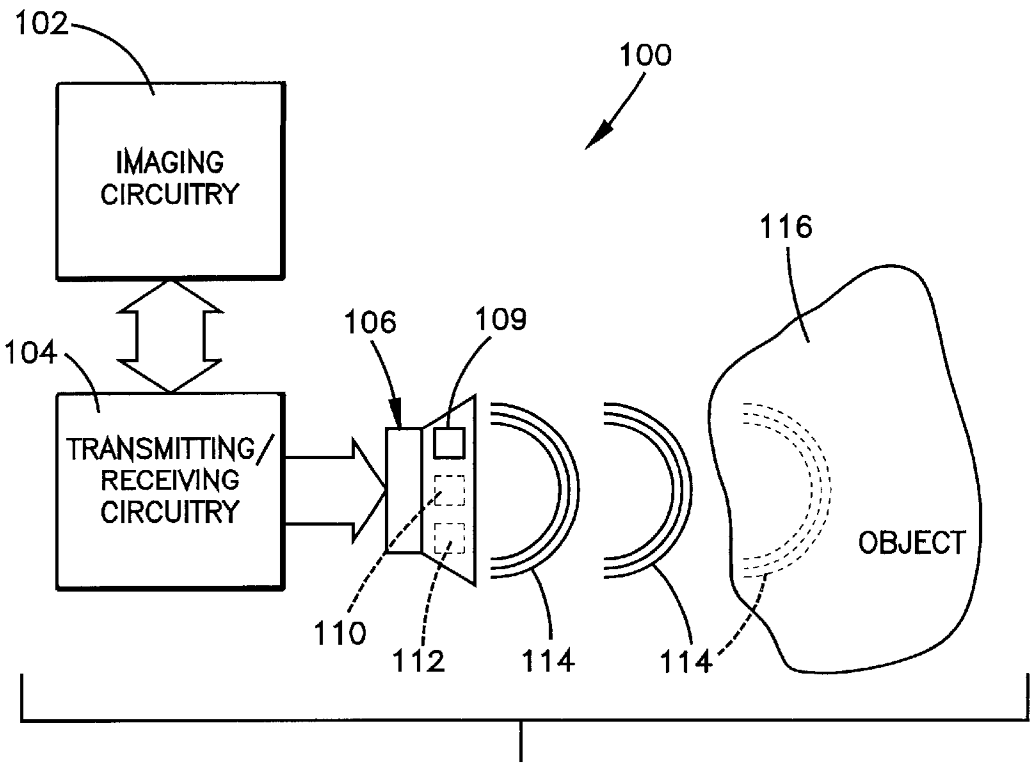
FIGS. 1 and 2 are block diagrams illustrating the operating principles of the present invention.
Figure 2:
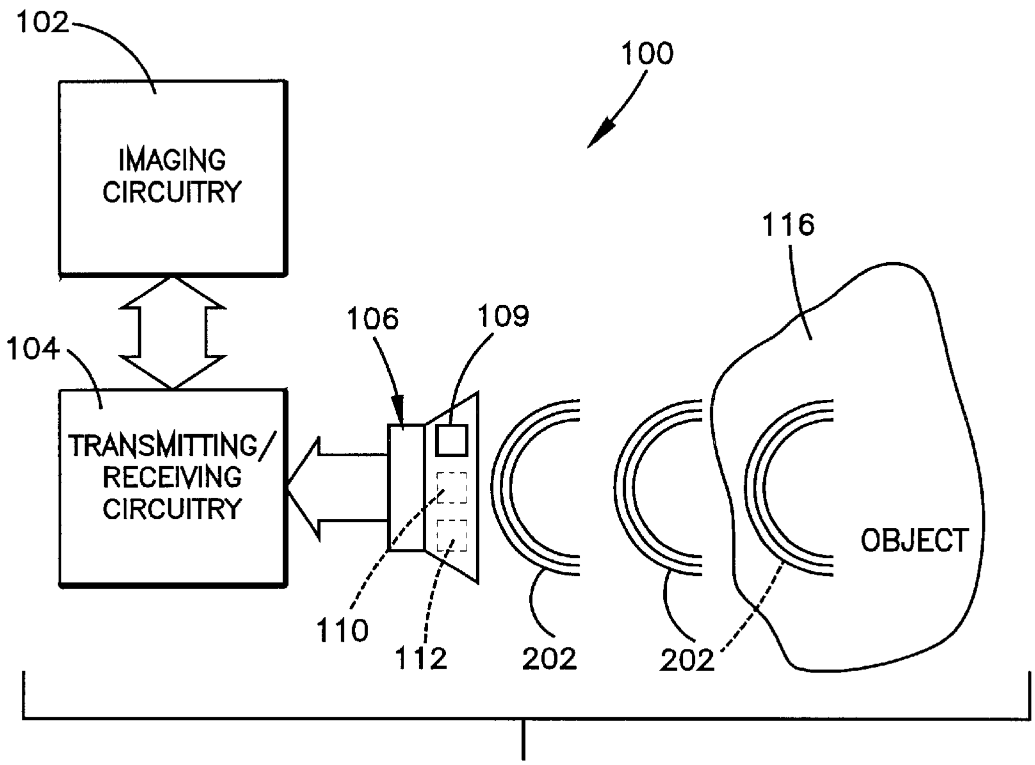

Referring to FIGS. 1 and 2, block diagrams of an ultrasound system 100 according to the present invention are shown. More specifically, FIG. 1 illustrates the system 100 during a sound wave emitting cycle and FIG. 2 illustrates the system 100 during a sound wave receiving cycle. The system 100 includes imaging circuitry 102, transmitting/receiving circuitry 104, and an ultrasound transducer 106. The imaging circuitry includes a computer based system (not shown) having appropriate logic or algorithms for driving and interpreting the sound echo information emitted and received from the transducer 106. The transmitting/receiving circuitry 104 includes interfacing components for placing the imaging circuitry 102 in circuit communication with the transducer 106. As described in more detail below, the transducer 106 has at least one transducing device 108, and optionally includes a plurality of such transducing devices as indicated by reference numbers 110 and 112. Each transducing device 108, 110, and 112 includes a transducing element and electronic circuitry for simplifying the communication between the transducer 106 and the imaging circuitry 102.

In operation, the imaging circuitry 102 drives the transducer 106 to emit sound waves 114 at a frequency in the range of 35 to 65 MHz. It should be understood that frequencies of any other desired range could also be emitted by the transducer 106. The sound waves 114 penetrate an object 116 to be imaged. As the sound waves 114 the penetrate object 116, the sound waves reflect off of interfaces between mechanically different structures within the object 116 and form reflected sound waves 202 illustrated in FIG. 2. The reflected sound waves 202 are received by the transducer 106. The emitted sound waves 114 and the reflected sound waves 202 are then used to construct an image of the object 116 through the logic and/or algorithms within the imaging circuitry 102.

Figure 3A:
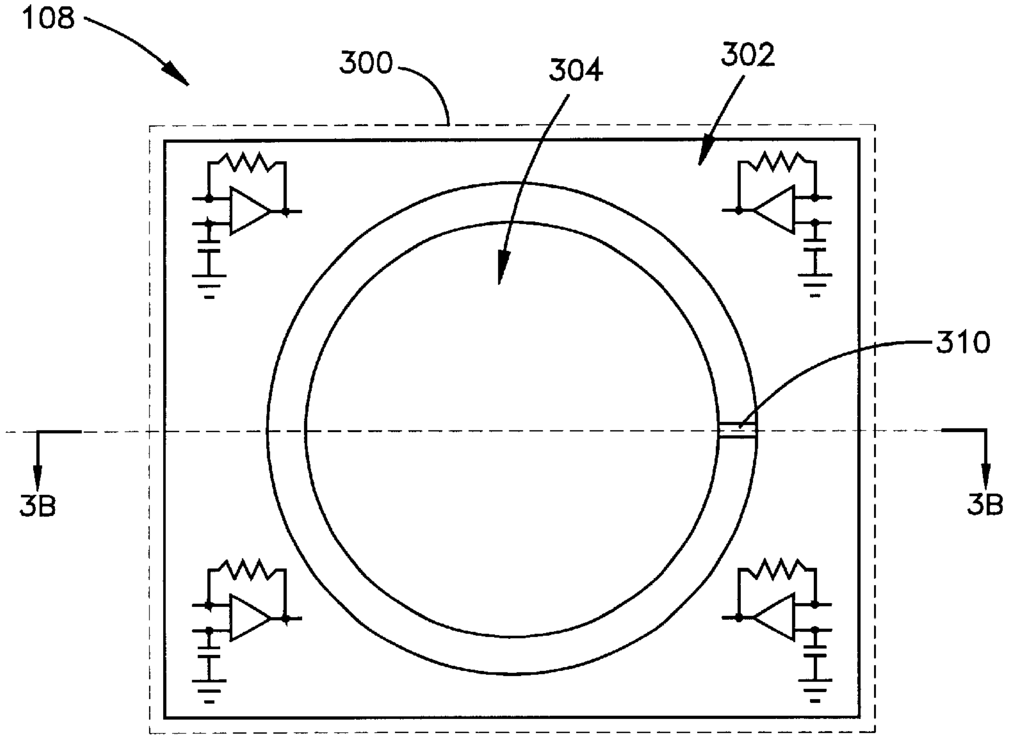
FIGS. 3A and 3B are illustrations of a first embodiment of an ultrasound transducer constructed in accordance with the present invention.
Figure 3B:
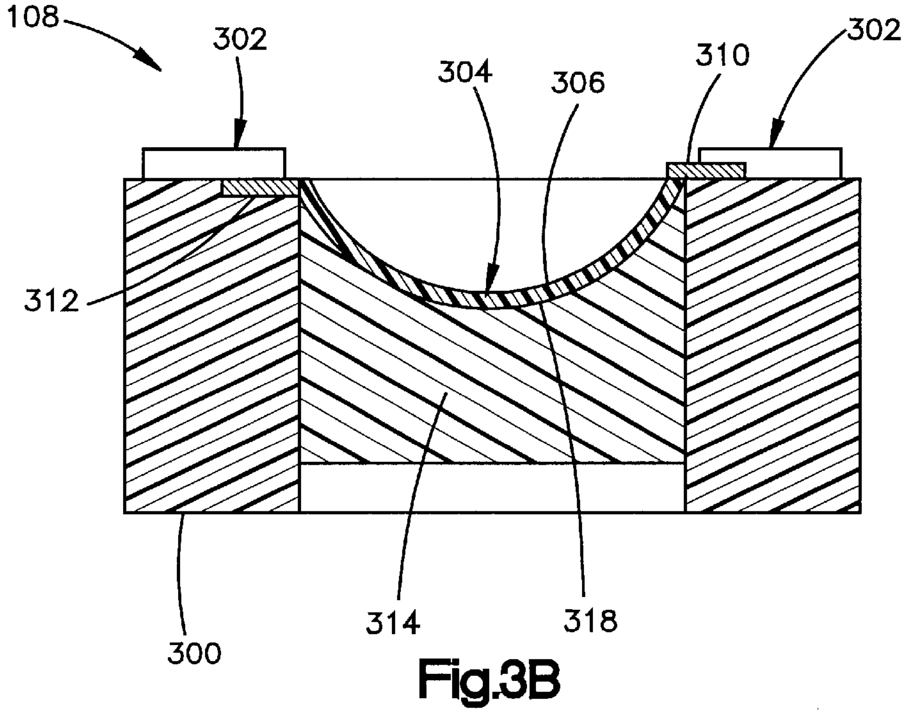

FIGS. 3A and 3B illustrate a first embodiment of the ultrasound transducing device 108 in plan view and in cross-sectional view, respectively. The transducing device 108 is formed on a substrate 300 that is approximately 1 $mm^3$ in size or smaller, although it should be understood that the transducing device 108 could be larger or smaller than 1 $mm^3$. The substrate 300 is made of silicon and has a topside and a backside surface. The topside surface has electronic circuitry 302 formed thereon. The electric circuitry 302 is formed through conventional processes such as Complementary Metal Oxide Silicon (CMOS) fabrication. The electronic circuitry 302 can include a large number of possible circuit designs and components including, but not limited to, signal conditioning circuitry, buffers, amplifiers, drivers, and analog-to-digital converters. The substrate 300 further has a hole or aperture 301 formed therein for receiving a diaphragm or transducing element 304. The aperture 301 is formed through either conventional Computer Numerical Control (CNC) machining, laser machining, micromachining, microfabrication, or a suitable MEMS fabrication process such as Deep Reactive Ion Etching (DRIE). The aperture 301 can be circular or another suitable shape, such as an ellipse.

The transducing element 304 is made of a thin film piezoelectric material, such as polyvinylidenefluoride (PVDF) or another suitable polymer. The PVDF film may include trifluoroethylene to enhance its piezoelectric properties. Alternatively, the transducing element 304 could be made of a non-polymeric piezoelectric material such as PZT or $Z_nO$. The PVDF film is spun and formed on the substrate 300. A free standing film could also be applied to the substrate 300 in lieu of the aforementioned spin coating process. The transducing element 304 can be between 1000 angstroms and 100 microns thick. In the illustrated embodiment, the transducing element 304 is approximately five to fifteen micrometers thick. However, as described below, the thickness of the transducing element 304 can be modified to change the frequency of the transducing device. The PVDF film is then made piezoelectric through corona discharge polling or similar methods.

The transducing element 304 has topside and backside surfaces 306 and 308, respectively. The topside surface 306 is in electrical communication with an electrode 310 and the backside surface 308 is in electrical communication with an electrode 312. The electrodes 310 and 312 provide an electrical pathway from the circuitry 302 to the transducing element 304. The electrodes 310 and 312 are formed, using a known micromachining, microfabrication, or MEMS fabrication technique such as surface micromachining, from conductive material such as a chrome-gold material or another suitable conductive material.

The transducing element 304 is capable of being mechanically excited by passing a small electrical current through the electrodes 310 and 312. The mechanical excitation generates sound waves at a particular frequency in the high-frequency or ultrasound range between 35 and 65 MHz. The exact frequency depends upon, among other things, the thickness of the transducing element 304 between the topside and backside surfaces 306 and 308, respectively. Hence, by controlling the thickness of the transducing element 304, the desired transducing frequency can be obtained. In addition to being excited by current passed through the electrodes 310 and 312, the transducing element 304 can also be mechanically excited by sound waves which then generate a current and/or voltage that can be received by the electrodes 310 and 312.

A binding material 314 preferably in the form of a potting epoxy is applied to the backside surface 308 of the transducing element 304. The binding material 314 is electrically conductive and mechanically maintains the shape of the transducing element 304. The binding material 314 also provides attenuation of sound emissions at the backside surface 308.

Figure 4A:
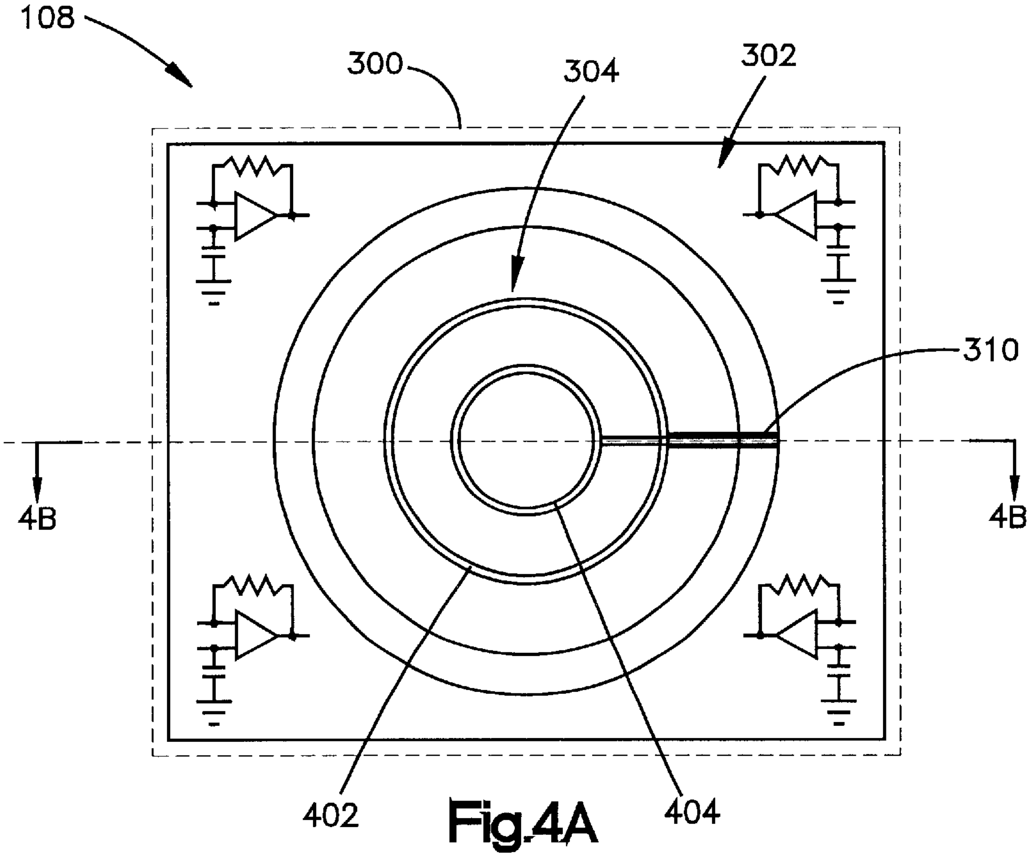
FIGS. 4A and 4B are illustrations of a second embodiment of an ultrasound transducer constructed in accordance with the present invention.
Figure 4B:
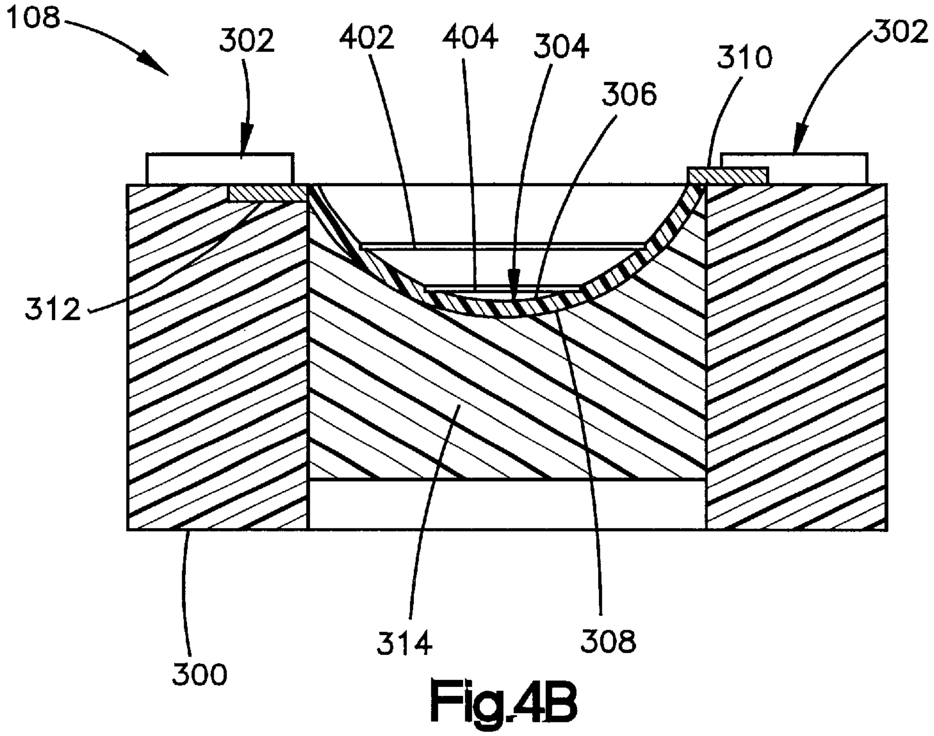

FIGS. 4A and 4B illustrate a second embodiment of the ultrasound transducing device 108 in plan view and in cross-sectional view, respectively. The second embodiment is substantially similar to the first embodiment of FIGS. 3A and 3B, except that the transducing device 108 according to the second embodiment includes one or more annular electrodes 402 and 404 operatively coupled between the electrodes 310 and 312. The annular electrodes 402 and 404 provide the transducing element 304 with the ability to form focused or directed sound waves. The annular electrodes 402 and 404 are made of standard metals and formed on the surface of the transducing element 304 by known microfabrication or MEMS fabrication techniques, such as photolithography, prior to deformation of the transducing element.

Figure 5:
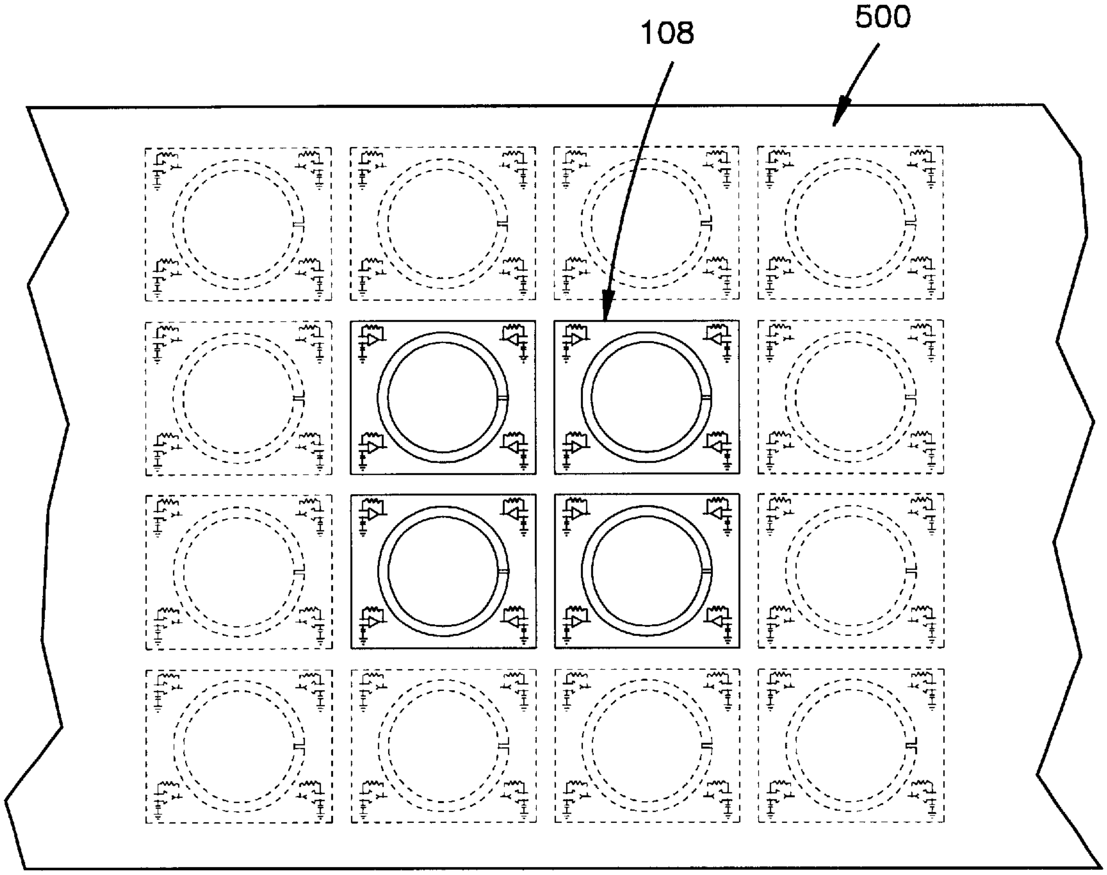
FIG. 5 is an illustration of a portion of a medical device having an array of ultrasound transducers according to the present invention.

Referring now to FIG. 5, an array 500 of ultrasound transducers 108 according to the present invention are shown. The array 500 can include transducers 108 of the variety shown in FIGS. 3A and 3B or FIGS. 4A and 4B, or combinations thereof. The array 500 is illustrated as being located on a probe for inserting into a human body, but could be located on a wide variety of other medical devices. An input and output bus (not shown) is coupled to each ultrasound transducer for carrying power, input, and output signals.

Referring now to FIGS. 6A through 6D, fabrication of the present invention will now be discussed. Before discussing the particulars, it should be noted that present invention is preferably fabricated on a wafer-scale approach. Nevertheless, less than wafer-scale implementation can also be employed such as, for example, on a discrete transducer level. The following description discusses a discrete transducer fabrication, but can also be implemented on a wafer-scale approach using known microfabrication, micromachining, or other MEMS fabrication techniques to produce several thousand transducers from a single four inch silicon wafer.

Figure 6A:
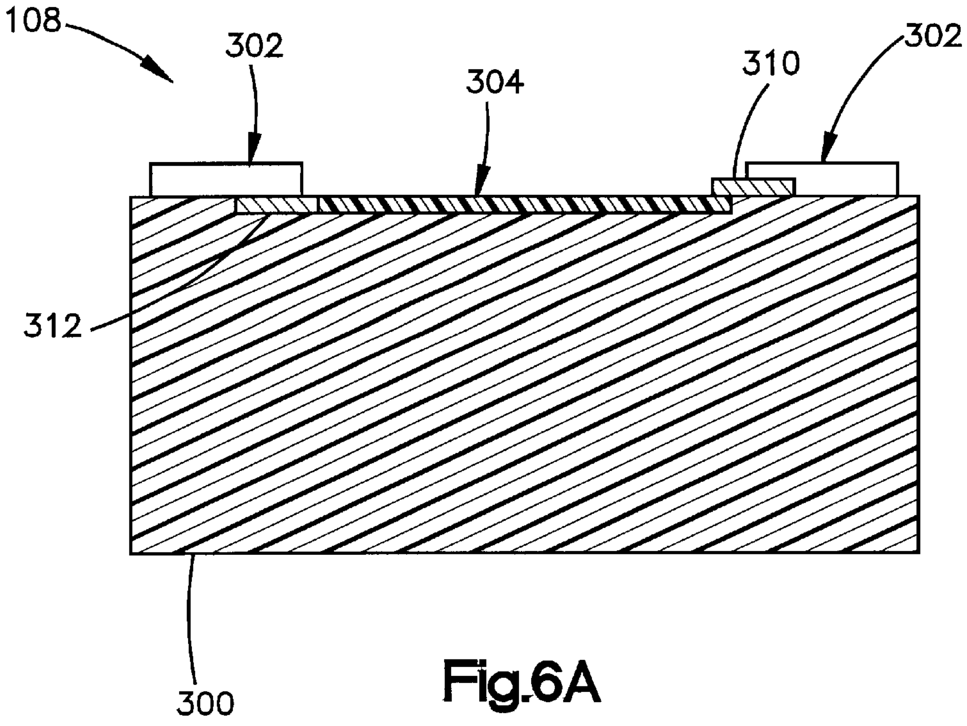
FIGS. 6A–6E illustrate the process of fabricating an ultrasound transducer in accordance with the present invention.

Referring now particularly to FIG. 6A, the substrate 300 is provided from a conventional circuit foundry with the desired circuitry 302 already fabricated thereon. The advantage of using substrates with circuitry already fabricated thereon is that existing circuit processing technologies can be used to form the required circuitry. The transducing element 304 is then spin-coated onto the substrate 300, followed by the metallization of a thin-film (not shown) thereon. The transducing element 304 is then "polled", via corona-discharge or similar method, to render the film piezoelectric.

Figure 6B:
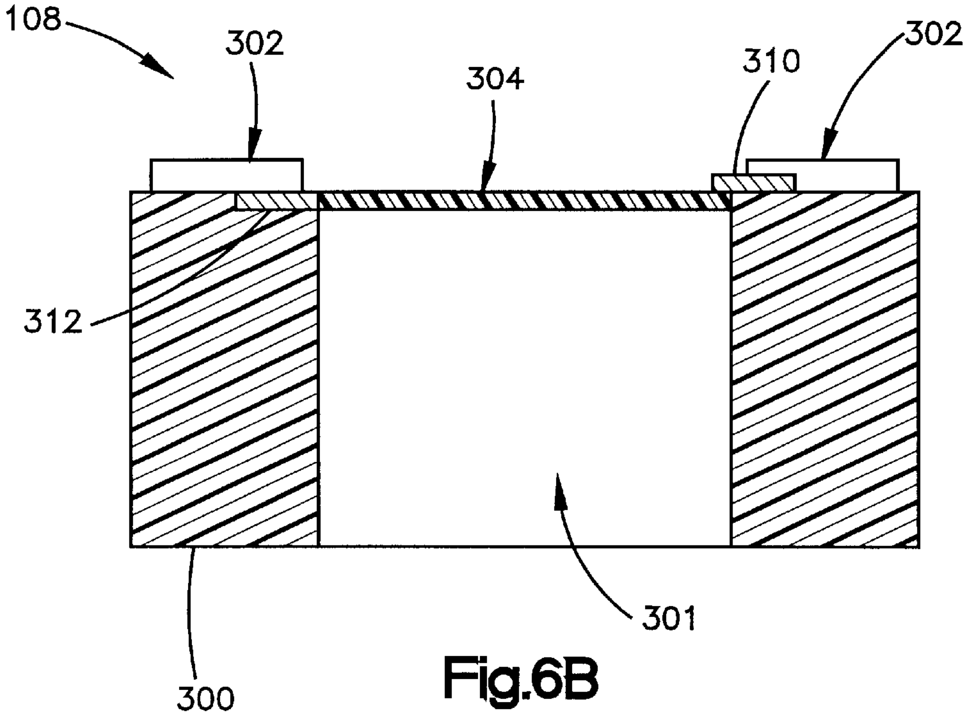
Figure 6C:
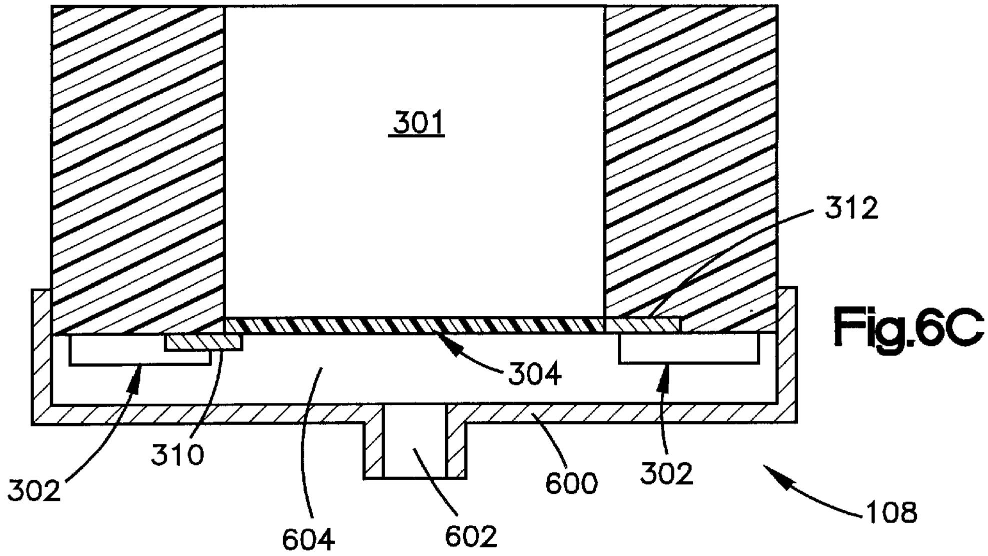
Figure 6D:
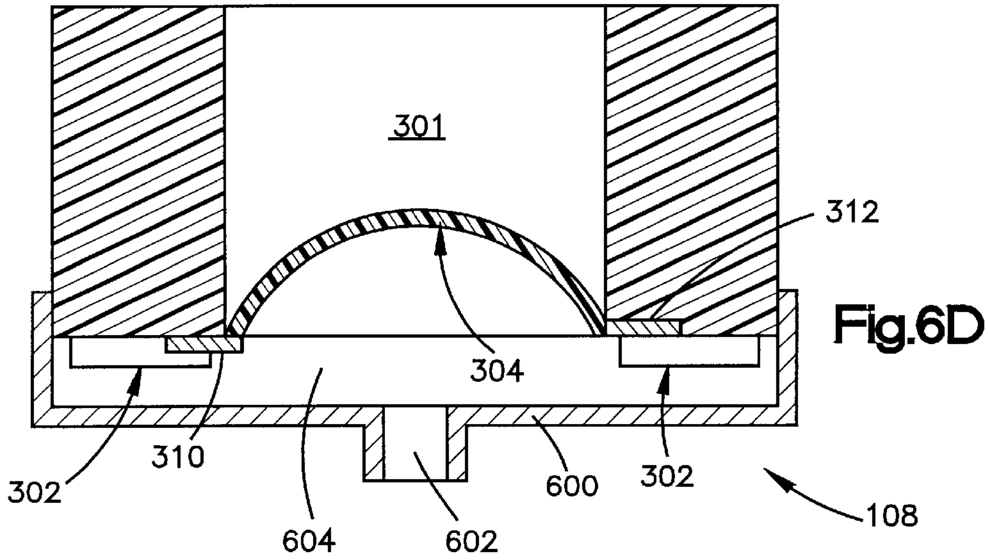

Referring now to FIG. 6B, the backside of the substrate 300 is machined away to form the aperture 301. The machining process can be conventional CNC machining, laser machining, micromachining, or a MEMS fabrication process such as DRIE. The transducing device 108 is then turned upside-down as shown in FIG. 6C. Next, a pressure jig 600 is placed over the now downwardly-facing surface of the substrate 300. The pressure jig 600 includes a pressure connection 602 and a vacuum space 604. The pressure connection 602 connects the pressure jig 600 to a source of pressurized air or other gas. The pressure jig 600 creates a seal against the substrate 300 and forms a pressurized space 604 for pressurizing the aperture 301. The pressurized space 604 permits the creation of a differential pressure across the transducing element 304 which causes the transducing element to be drawn into the aperture 301. As shown in FIG. 6D, the differential pressure results in the transducing element 304 being deformed from a planar shape into an arcuate shape that is a substantially spherical section. The spherical section shape of the transducer element 304 is preferably less than hemispherical as may be seen in FIG. 6D, but could be hemispherical or another shape.

Figure 6E:
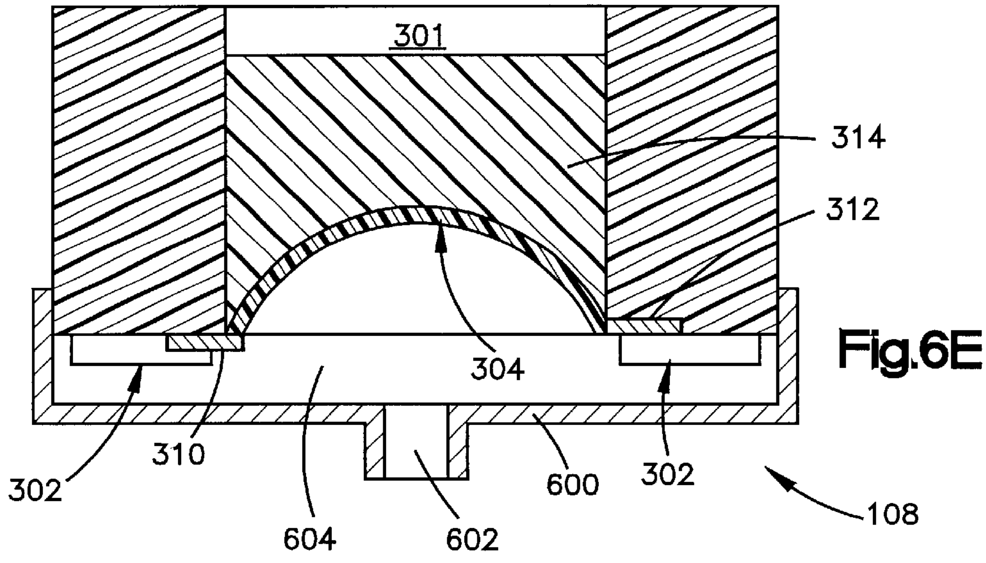

It should be understood that the pressure jig 600 shown in FIGS. 6C–6E could be a portion of a larger jig for performing simultaneous pressurization of hundreds or even thousands of transducing devices 108 formed on a single silicon wafer.

Referring now to FIG. 6E, the binding material 314 is introduced into the aperture 301. The binding material 314 can be any shape once applied. The binding material 314 is a fluid or semi-solid when applied to the backside surface 308 of the transducing element 304 and the contacts the walls of the aperture 301 in the substrate 300. The binding material 314 subsequently dries to a solid. The binding material 314 is a suitable form of potting epoxy, which can be either conductive or nonconductive. As described, the binding material 314 functions to maintain the substantially hemispheric shape of transducing element 304. The binding material 314 further acts to absorb sound waves generated by transducing element 304 that are not used in the imaging process.

Figure 6F:
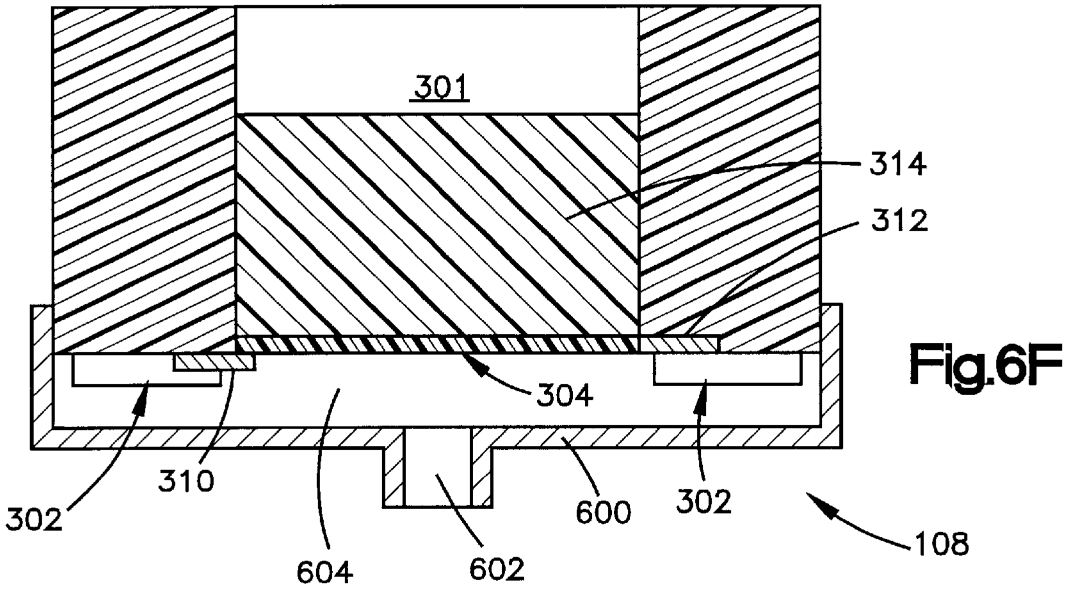
FIGS. 6F and 6G illustrate an alternate process for fabricating an ultrasonic transducer in accordance with the present invention.
Figure 6G:
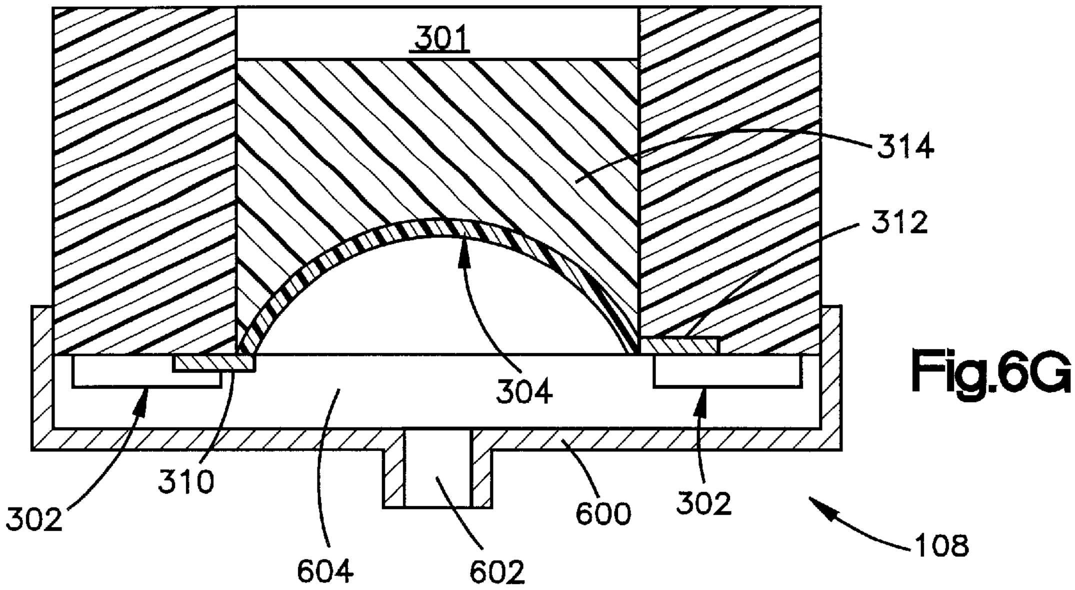
Figure 7A:
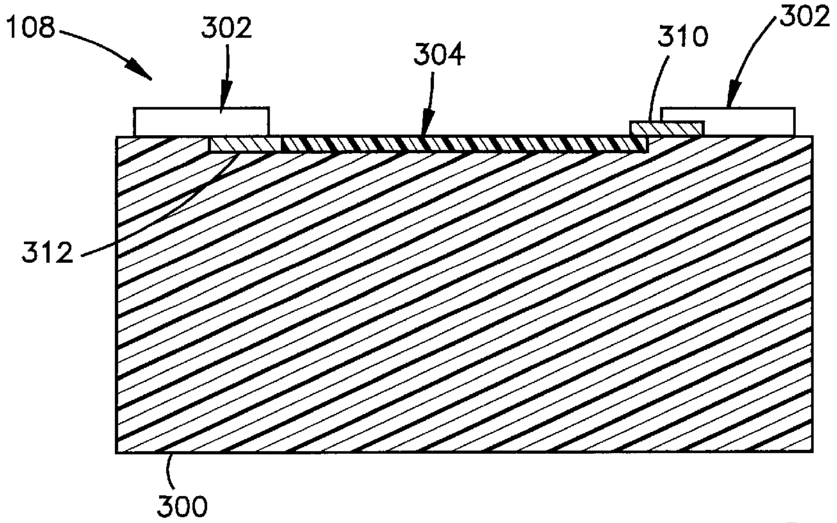
FIGS. 7A–7E illustrate another alternate process for fabricating an ultrasonic transducer in accordance with the present invention.
Figure 7B:
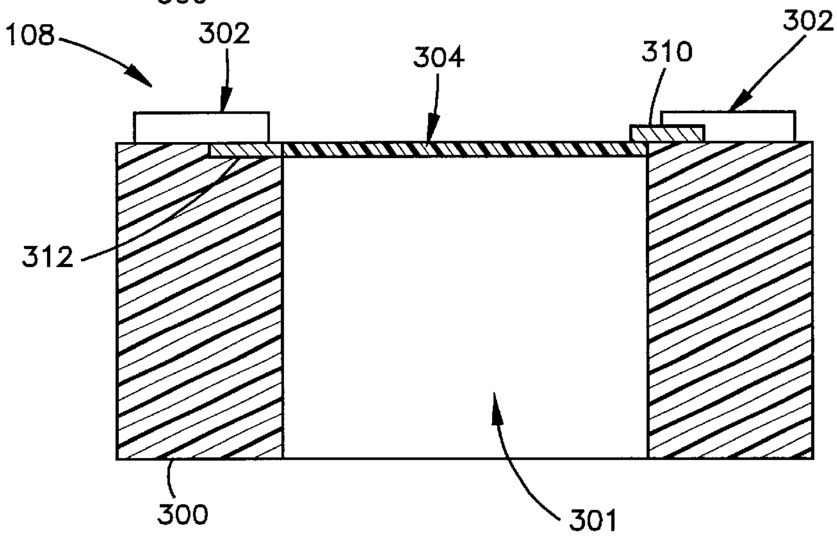
Figure 7C:
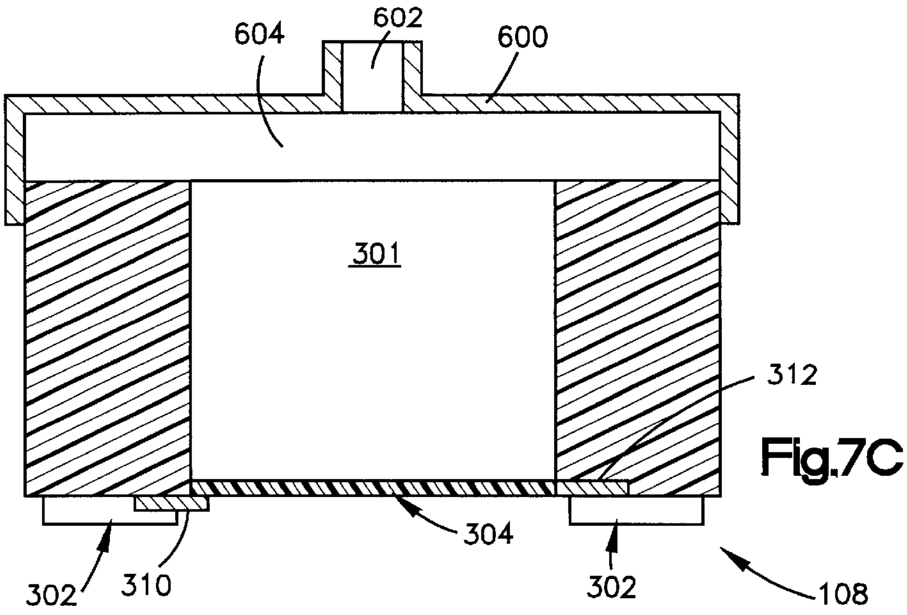
Figure 7D:
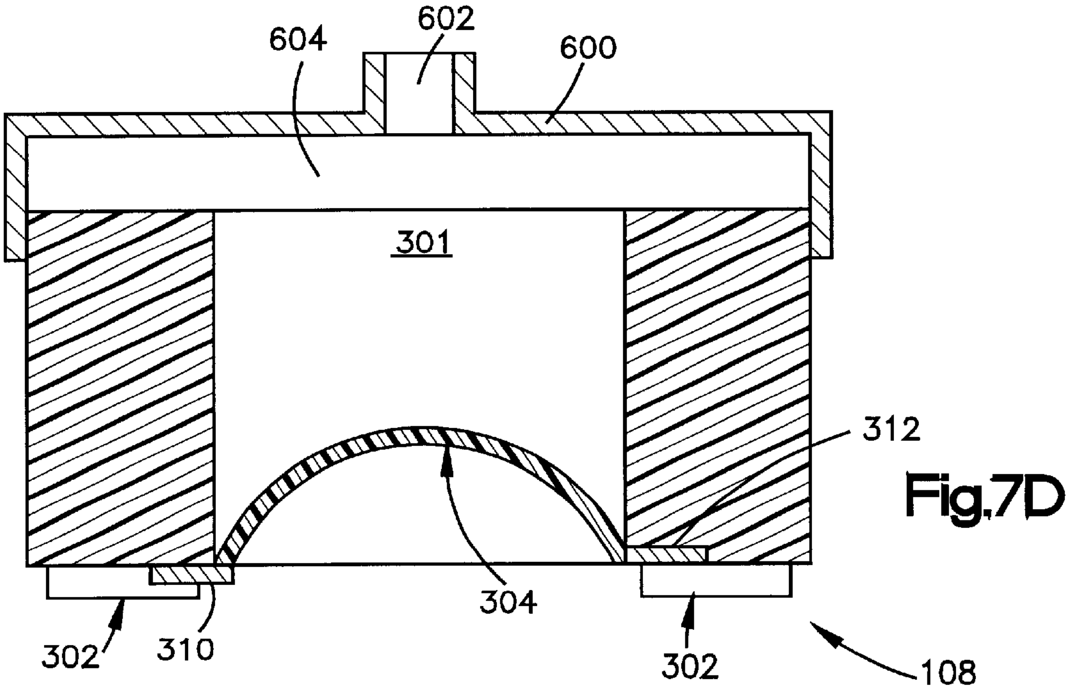
Figure 7E:
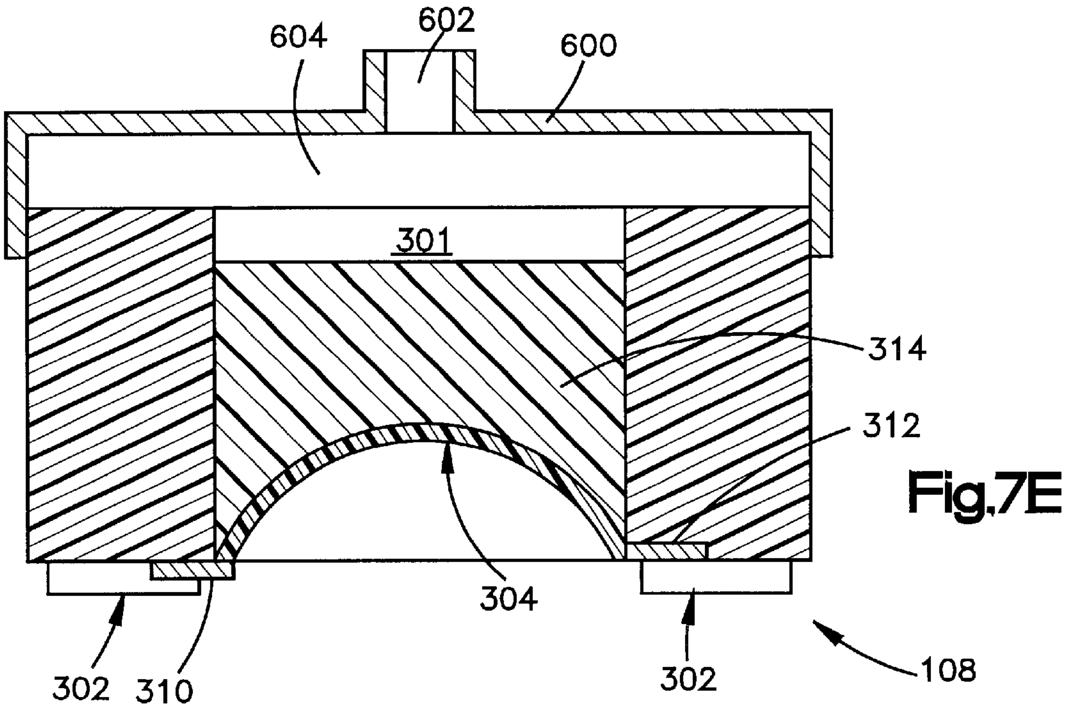

FIGS. 6F and 6G illustrate an alternate process for fabricating the ultrasonic transducing device 108. The alternate process shown on FIGS. 6F and 6G is similar to the process steps shown in FIGS. 6C–6E, except that the binding material 314 is placed in the aperture 301 behind the transducing element 304 before, rather than after, the differential pressure is applied to the transducing element by the pressure jig 600. The liquid or semi-solid binding material 314 is then deflected along with the transducing element 304 by the differential pressure and, once solidified, mechanically supports the transducing element.

FIGS. 7A–7E illustrate another alternate process for fabricating the ultrasonic transducing device 108. The alternate process of FIGS. 7A–7F is similar to the process shown in FIGS. 6A–6E, except that the pressure jig 600 brought down over the upwardly-facing surface of the substrate 300 and the pressure source 602 pulls a vacuum, rather than applying increased pressure, in the aperture 301 to cause the desired deflection of the transducing element 304. Once the transducing element 304 is deflected as desired, the binding material 314 is applied as discussed previously.

Figure 8A:
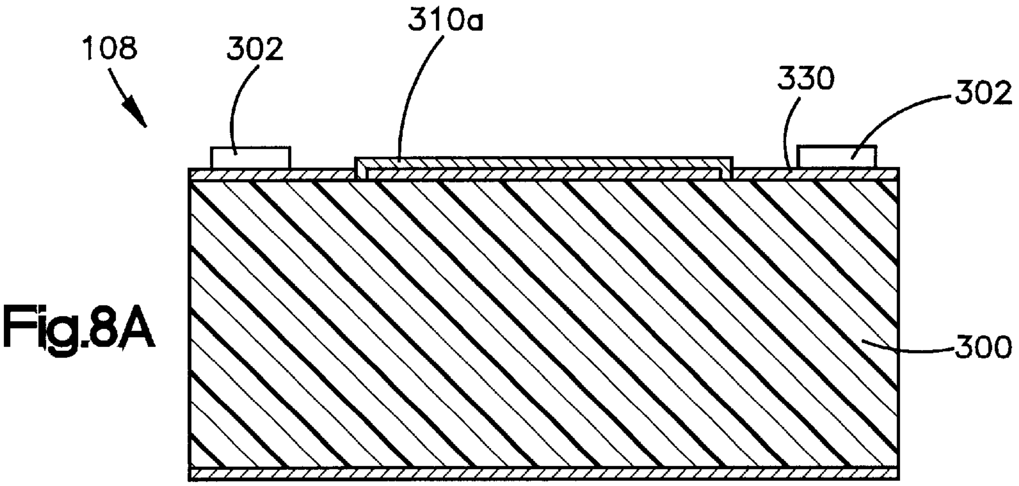
FIGS. 8A–8H illustrate yet another alternate process for fabricating an ultrasonic transducer in accordance with the present invention.
Figure 8B:
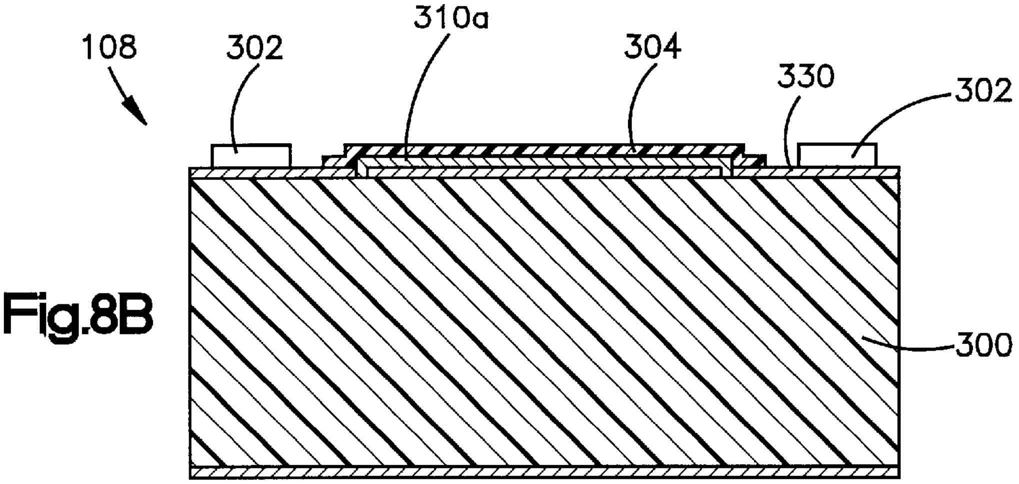
Figure 8C:
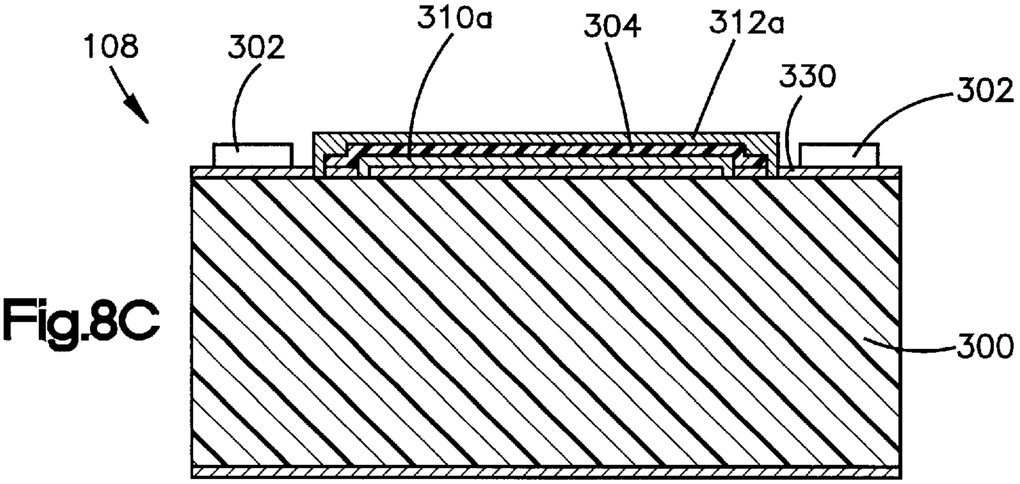

FIGS. 8A–8E illustrate another alternate process for fabricating the ultrasonic transducing device 108. In FIGS. 8A–8E, components that are similar to components shown in FIGS. 6A–6E use the same reference numbers, but are identified with the suffix "a". Referring now particularly to FIG. 8A, the silicon substrate 300 is provided from a conventional circuit foundry and the desired circuitry 302 already fabricated thereon. The substrate 300 is already coated with a field oxide layer 330 which is then used to pattern the electrodes 310*a* and 312*a* (FIG. 8C) on the substrate. After the electrode 310*a* is deposited on the substrate 300 and operatively coupled to the circuitry 302, the transducing element 304 is then spin-coated over the electrode 310*a*, as shown in FIG. 8B. The electrode 312*a* is then deposited over the transducing element 304, as shown in FIG. 8C.

Figure 8D:
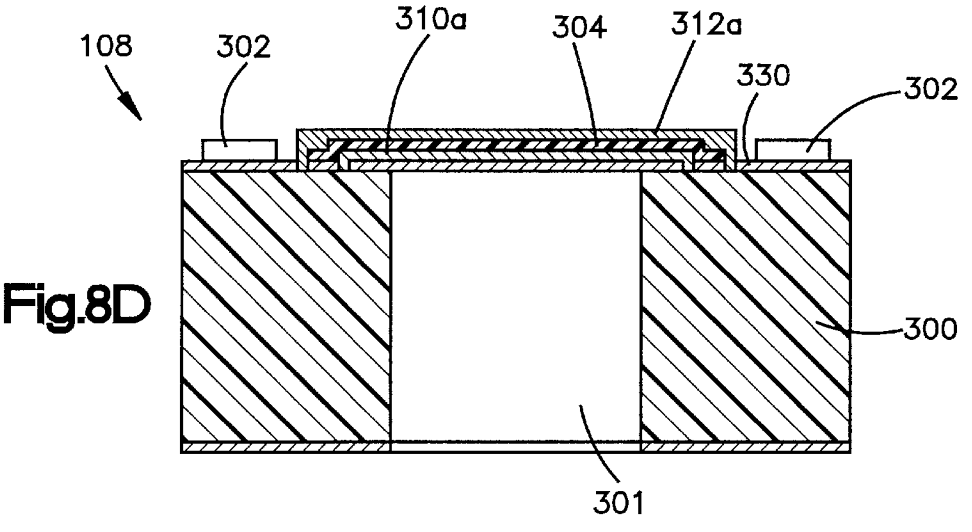
Figure 8E:
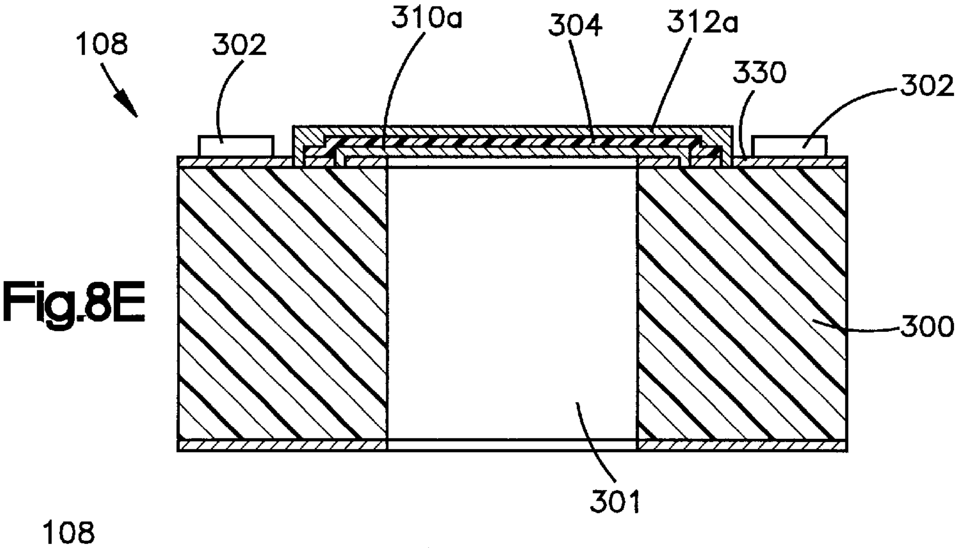

Referring now to FIG. 8D, the backside of the substrate 300 is etched, using a DRIE process, to form the aperture 301. A second etching process is then employed to remove the oxide inside the aperture 301 (FIG. 8E).

Figure 8F:
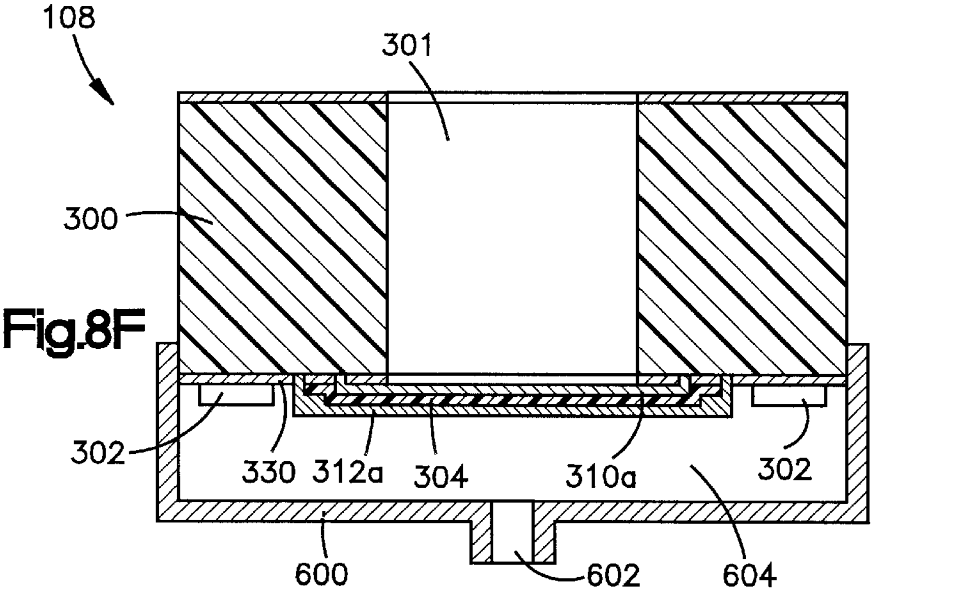
Figure 8G:
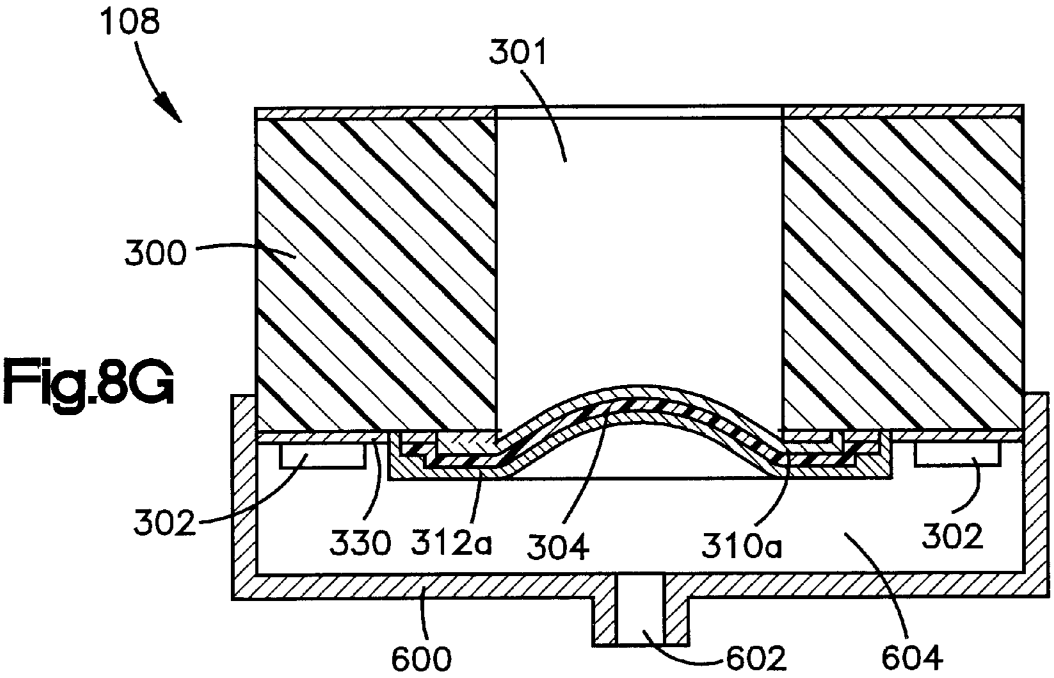

The transducing device 108 is then turned upside-down as shown in FIG. 8F. Next, a pressure jig 600 is placed over the now downwardly-facing surface of the substrate 300. The pressure jig 600 includes a pressure connection 602 and a vacuum space 604. The pressure connection 602 connects the pressure jig 600 to a source of pressurized air or other gas. The pressure jig 600 creates a seal against the substrate 300 and forms a pressurized space 604 for pressurizing the aperture 301. The pressurized space 604 permits the creation of a differential pressure across the transducing element 304 which causes the transducing element to be drawn into the aperture 301. As shown in FIG. 8G, the differential pressure results in the transducing element 304 being deformed from a planar shape into an arcuate shape that is a substantially spherical section. The spherical section shape of the transducer element 304 is preferably less than hemispherical as may be seen in FIG. 6G, but could be hemispherical or another shape. The transducing element 304 is then "polled", via corona-discharge or similar method, to render the film piezoelectric.

It should be understood that the pressure jig 600 shown in FIGS. 8F–8G could be a portion of a larger jig for performing simultaneous pressurization of hundreds or even thousands of transducing devices 108 formed on a single silicon wafer.

Figure 8H:
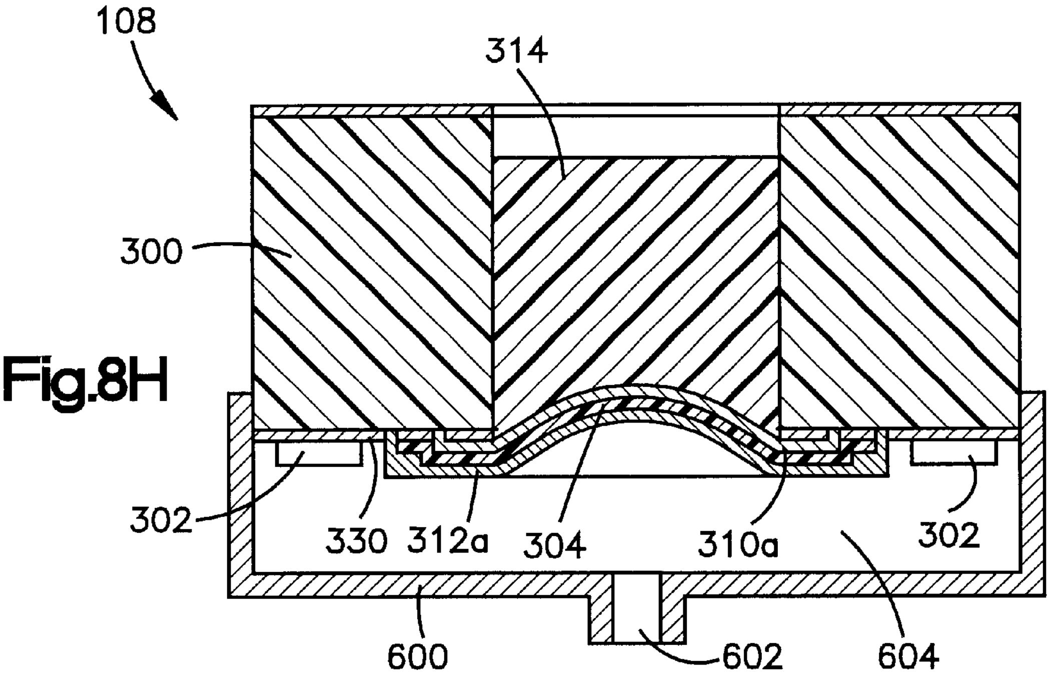

Referring now to FIG. 8H, the binding material 314 is introduced into the aperture 301. The binding material 314 can be any shape once applied. The binding material 314 is a fluid or semi-solid when applied to the backside surface 308 of the transducing element 304 and the contacts the walls of the aperture 301 in the substrate 300. The binding material 314 subsequently dries to a solid. The binding material 314 is a suitable form of potting epoxy and should be non-conductive. As described, the binding material 314 functions to maintain the substantially hemispheric shape of transducing element 304. The binding material 314 further acts to absorb sound waves generated by transducing element 304 that are not used in the imaging process.

From the above description of the invention, those skilled in the art will perceive improvements, changes and modifications. For example, it is contemplated that the shape of the transducing element 304 could be a section of an ellipse, rather than a section of a sphere, in order to provide a different focus for the transducing device 108 and/or alter the frequency of the transducing device. Such an elliptical section shape could be produced by varying the configuration of the aperture 301 in the substrate 300 or by varying the thickness of the transducing element 304. Further, the annular electrodes 402 and 404 could also be formed to have a shape that is a section of an ellipse. Such improvements, changes and modifications within the skill of the art are intended to be covered by the appended claims.

Having described the invention, we claim:

1. An ultrasonic transducer for use in medical imaging, said ultrasonic transducer comprising:

a substrate having oppositely disposed first and second outer surfaces, said substrate including an aperture extending from said first outer surface to said second outer surface;

a diaphragm positioned at least partially within said aperture, said diaphragm having an arcuate shape that is a section of a sphere for focusing ultrasonic waves emitted from the diaphragm;

a plurality of electrodes in physical communication with said diaphragm; and a binder material in physical communication with said diaphragm and said substrate.

2. The ultrasonic transducer of claim 1 wherein said diaphragm comprises a thin film piezoelectric material.

3. The ultrasonic transducer of claim 2 wherein said thin film piezoelectric material is a polyvinylidenefluoride film.

4. The ultrasonic transducer of claim 2, wherein said thin film piezoelectric material is film comprising polyvinylidenefluoride and trifluoroethylene.

5. The ultrasonic transducer of claim 1 wherein said diaphragm comprises a free-standing film.

6. The ultrasonic transducer of claim 1 wherein said binding material comprises a conductive material.

7. The ultrasonic transducer of claim 1 wherein said binding material comprises a non-conductive material.

8. The ultrasonic transducer of claim 1 wherein said binder material is located at least partially within said aperture, said binder material abutting and supporting said diaphragm and attenuating sound waves generated by said diaphragm.

9. The ultrasonic transducer of claim 1 wherein said diaphragm has a thickness between 1000 angstroms and 100 microns.

10. The ultrasonic transducer of claim 9 wherein said diaphragm has a thickness of approximately five to fifteen micrometers.

11. The ultrasonic transducer of claim 1 wherein at least one of said plurality of electrodes is an annular electrode formed on a surface of said diaphragm and operative to further focus emitted sound waves.

12. The ultrasonic transducer of claim 1 wherein said diaphragm resonates at a frequency between 30 and 120 Mhz.

13. The ultrasonic transducer of claim 1 wherein said first surface of said substrate comprises a surface area of about 1 $mm^2$.

14. The ultrasonic transducer of claim 1 wherein said substrate is fabricated from silicon.

15. A method for forming an ultrasonic transducer comprising the steps of:

providing a silicon substrate, having oppositely disposed first and second outer surfaces;

creating an aperture in the substrate extending from the first surface to the second surface via a micromachining, microfabrication, or MEMS fabrication process;

covering the aperture with a film;

forming a plurality of electrodes in physical communication with the film via a micromachining, microfabrication, or MEMS fabrication process;

applying a differential pressure across the film to form a diaphragm having a shape that is a section of a sphere; and applying binding material to the diaphragm to maintain the spherical section shape of the diaphragm.

16. The method of claim 15 wherein the electrodes are formed via surface micromachining.

17. The method of claim 15 wherein the aperture is provided via deep reactive ion etching.

18. The method of claim 15 wherein the step of applying binding material is done before the differential pressure is applied.

19. The method of claim 15 wherein the step of applying binding material is done after the differential pressure is applied.

20. The method of claim 15 further comprising the step of:

forming at least one annular electrode on a surface of the diaphragm.

21. The method of claim 15 further comprising the step of:

rendering the diaphragm piezoelectric.

22. The method of step 21 where the step of rendering the diaphragm piezoelectric comprises corona discharge polling of the diaphragm.

23. A medical device for insertion into a mammalian body, said medical device comprising:

an insertable body portion; and an ultrasonic transducing section on said insertable body portion, said ultrasonic transducing section having at least one ultrasonic transducer, each of said at least one ultrasonic transducer comprising:

a substrate having oppositely disposed first and second outer surfaces, said substrate including an aperture extending from said first outer surface to said second outer surface;

a diaphragm positioned at least partially within said aperture, said diaphragm having an arcuate shape that is a section of a sphere for focusing ultrasonic waves emitted from said diaphragm;

a plurality of electrodes in physical communication with said diaphragm; and a binder material in physical communication with said diaphragm and said substrate.

24. The medical device of claim 23 wherein said diaphragm comprises a thin film piezoelectric material.

25. The medical device of claim 24, wherein said thin film piezoelectric material is a polyvinylidenefluoride film.

26. The medical device of claim 24, wherein said thin film piezoelectric material is a film comprising polyvinylidenefluoride and trifluoroethylene.

27. The medical device of claim 23 wherein said diaphragm comprises a free-standing film.

28. The medical device of claim 23 wherein said binding material comprises a conductive material.

29. The medical device of claim 23 wherein said binding material comprises a non-conductive material.

30. The medical device of claim 23 wherein at least one of said plurality of electrodes is an annular electrode formed on a surface of said diaphragm and operative to further focus sound waves emitted by said at least one transducer.

31. The medical device of claim 23 wherein said binder material is located at least partially within said aperture, said binder material abutting and supporting said diaphragm and attenuating sound waves generated by said diaphragm.

32. The medical device of claim 23 wherein said first surface of said substrate comprises a surface area of about 1 $mm^2$.

33. The medical device of claim 23 wherein said substrate is fabricated from silicon.

* * * * *

UNITED STATES PATENT AND TRADEMARK OFFICE

CERTIFICATE OF CORRECTION

PATENT NO. : 6,641,540 B2
APPLICATION NO. : 09/948068
DATED : November 4, 2003
INVENTOR(S) : Aaron J. Fleischman, Shuvo Roy and Geoffrey R. Lockwood It is certified that error appears in the above-identified patent and that said Letters Patent is hereby corrected as shown below:

Column 8, line 3, after “wherein” delete “the electrodes are formed” and insert --said forming of electrodes is achieved--.

Column 8, line 5, after “wherein” delete “the aperture is provided via deep reactive ion etching” and insert --an etching of deep reactive ion creates the aperture--.

Signed and Sealed this

Ninth Day of January, 2007

JON W. DUDAS
*Director of the United States Patent and Trademark Office*